United States Patent [19]

Breidenbach et al.

[11] 4,419,513
[45] Dec. 6, 1983

[54] ISOCYANATO-ISOCYANURATES, AND PROCESS FOR THE PRODUCTION THEREOF

[75] Inventors: Peter Breidenbach, Cologne; Manfred Bock, Leverkusen; Josef Pedain, Cologne; Gerhard Mennicken, Leverkusen, all of Fed. Rep. of Germany

[73] Assignee: Bayer Aktiengesellschaft, Leverkusen, Fed. Rep. of Germany

[21] Appl. No.: 296,677

[22] Filed: Aug. 27, 1981

[30] Foreign Application Priority Data

Sep. 9, 1980 [DE] Fed. Rep. of Germany ....... 3033860

[51] Int. Cl.$^3$ .......................................... C07D 251/34
[52] U.S. Cl. .................................................... 544/222
[58] Field of Search ........................................ 544/222

[56] References Cited

U.S. PATENT DOCUMENTS

| | | | |
|---|---|---|---|
| 2,801,244 | 7/1957 | Belou | 260/248 |
| 3,367,934 | 2/1968 | Tate et al. | 260/248 |
| 3,394,111 | 7/1968 | Liebsch | 260/775 |
| 3,641,024 | 2/1972 | Argabright et al. | 544/222 |
| 3,645,979 | 2/1972 | Liebsch et al. | 260/775 |
| 3,919,218 | 11/1975 | Schmitt et al. | 544/222 |
| 4,059,610 | 11/1977 | Handa et al. | 544/222 |
| 4,246,132 | 1/1981 | Gras et al. | 544/222 |
| 4,255,569 | 3/1981 | Muller et al. | 544/222 |
| 4,324,879 | 4/1982 | Bock et al. | 544/193 |

FOREIGN PATENT DOCUMENTS

| | | |
|---|---|---|
| 882191 | 9/1971 | Canada . |
| 10589 | 8/1979 | European Pat. Off. . |
| 2616415 | 11/1977 | Fed. Rep. of Germany . |
| 2644684 | 4/1978 | Fed. Rep. of Germany . |
| 2724914 | 12/1978 | Fed. Rep. of Germany . |
| 2726749 | 1/1979 | Fed. Rep. of Germany . |
| 2806731 | 8/1979 | Fed. Rep. of Germany . |
| 2901479 | 7/1980 | Fed. Rep. of Germany . |
| 1576795 | 6/1969 | France . |
| 809809 | 11/1957 | United Kingdom . |
| 952931 | 3/1964 | United Kingdom . |
| 1571933 | 4/1977 | United Kingdom . |

*Primary Examiner*—John M. Ford
*Attorney, Agent, or Firm*—Gene Harsh; Lawrence S. Pope; Thomas W. Roy

[57] ABSTRACT

The present invention relates to a process for the preparation of novel isocyanato-isocyanurates by the catalytic and 1-isocyanato-3,3,5-trimethyl-5-isocyanatomethyl-cyclohexane in a mole ratio of about 1:4 to 4:1, and to the products produced therefrom.

The present invention also relates to the use of these products, optionally in blocked form, as the isocyanate component in polyurethane lacquers.

13 Claims, No Drawings

ISOCYANATO-ISOCYANURATES, AND PROCESS FOR THE PRODUCTION THEREOF

BACKGROUND OF THE INVENTION

1. Field of the Invention

The present invention relates to new isocyanurates having isocyanate groups, based on mixtures of hexamethylene diisocyanate and 1-isocyanato-3,3,5-trimethyl-5-isocyanatomethyl-cyclohexane (isophorone diisocyanate or IPDI), to a process for the production thereof by the catalytic trimerization of a mixture of the above-mentioned diisocyanates and to the use thereof as isocyanate component in polyurethane lacquers.

2. Description of the Prior Art

The preparation of isocyanurates having isocyanate groups by the catalytic trimerization of some of the isocyanate groups of organic diisocyanates is known from numerous publications (see, for example, British Pat. Nos. 809,809 or 856,372; German Pat. No. 1,201,992, German Offenlegungsschrift Nos. 1,644,809; 1,670,667; 2,616,415; 2,616,416; 2,644,684; 2,724,914; 2,726,749; and 2,806,731; U.S. Pat. Nos. 2,801,244 and 3,394,111 or Published European Application No. 10589).

The isocyanurates having isocyanate groups prepared according to these prior art processes are valuable starting materials, in particular for the production of two-component polyurethane lacquers, in which they may be advantageously used as isocyanate component. The isocyanato-isocyanurates having aromatically-bound isocyanurate groups are particularly suitable for the production of lacquers of great hardness and elasticity, while the isocyanato-isocyanurates having aliphatically- or cycloaliphatically-bound isocyanate groups are particularly used for the production of weatherproof, light-fast lacquers. The isocyanato-isocyanurates described in the above-mentioned publications having aliphatically- or cycloaliphatically-bound isocyanate groups still suffer, however, from the disadvantage that they cannot simultaneously meet all of the practical requirements. For example, the isocyanato-isocyanurates based on aliphatic diisocyanates, such as hexamethylene diisocyanate, are not always suitable for uses which are steadily increasing in scope and significance, which uses require a good solubility in slightly polar, physiologically harmless solvents (e.g. petroleum fractions), because for the preparation of the solutions, more polar solvents must be simultaneously used or because the dilutability of the solutions is restricted by the above-mentioned non-polar solvents.

Moreover, these isocyanato-isocyanurates are usually liquid (even in blocked form) and for this reason, are unsuitable for use in powder lacquers. In addition thereto, lacquers which are produced using these polyisocyanates usually exhibit a low initial hardness which impairs the rapid further processing thereof.

Isocyanato-isocyanurates which are obtained by trimerizing cycloaliphatic diisocyanates do indeed exhibit good solubilities in slightly polar solvents, but in turn require considerable quantities of these solvents for the preparation of solutions of conventional processing viscosities. This fact considerably restricts the usefulness thereof in low solvent systems.

The products do have softening points which are clearly above room temperature. However, they impart to the resulting coatings a certain brittleness and a restricted elasticity which limits the use thereof particularly in lacquers, on which are imposed exacting requirements with respect to elasticity even at low temperatures.

Surprisingly, it has now been found that the isocyanato-isocyanurates according to the present invention and described in detail below, based on hexamethylene diisocyanate and IPDI, compare advantageously with the isocyanato-isocyanurates described in the above-mentioned publications by virtue of the favorable property spectrum thereof. The compounds or mixtures according to the present invention may be dissolved into clear, highly concentrated, low viscosity solutions in slightly polar solvents which may be further diluted as required using the same solvents without cloudiness occurring. The lacquers produced using the compounds or mixtures according to the present invention are also distinguished by a desirable hardness and outstanding elasticity of the resulting lacquer even at low temperatures.

This observation is surprising, although there is also the passing reference in some of the above references, for example in British Pat. No. 809,809 or in German Offenlegungsschrift Nos. 2,644,684; 2,724,914 or 2,726,749, after enumerating long lists of suitable aliphatic or cycloaliphatic diisocyanates, that mixtures of the isocyanates mentioned may also be used. However, from this reference alone, the skilled man could not infer any suggestion whatsoever of selecting hexamethylene diisocyanate and IPDI from this list in order to prepare mixed trimers from these two diisocyanates. In fact, there is no concrete indication in the above-mentioned publications of choosing these two-diisocyanates.

SUMMARY OF THE INVENTION

The present invention is directed to compounds or mixtures of compounds corresponding to the following general formula:

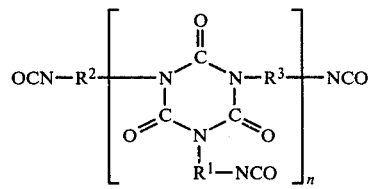

wherein
R$^1$, R$^2$ and R$^3$, which may be the same or different, represent a hexamethylene radical or a radical obtainable by removing the isocyanate groups from 1-isocyanato-3,3,5-trimethyl-5-isocyanatomethyl-cyclohexane, such that (on statistical average) at least about 20% and at the most about 80% of the radicals R$^1$, R$^2$ and R$^3$ represent a hexamethylene radical; and n represents an integer or (on statistical average) a fractional number of from about 1 to 7.

The present invention is additionally directed to a process for the preparation of the compounds or mixtures according to the present invention by trimerizing a part of the isocyanate groups of a diisocyanate mixture consisting essentially of aliphatic and cycloaliphatic diisocyanates, in the presence of catalysts accelerating the trimerization of isocyanate groups, by stopping the trimerization reaction as soon as from about 10 to 60% of the isocyanate groups which were originally present have been trimerized, by deactivating the catalyst used by heating the reaction mixture to a temperature above the decomposition temperature of the catalyst and/or by adding a catalyst poison, and optionally removing the non-reacted excess isocyanate by thin layer distillation, characterized in that a mixture of hexamethylene diisocyanate and 1-isocyanato-3,3,5-trimethyl-5-isocyanato-methyl-cyclohexane is used in a mole ratio of from about 4:1 to 1:4.

The present invention is further directed to the use of the compounds or mixtures according to the present invention, optionally blocked by isocyanate blocking agents, as the isocyanate component in polyurethane lacquers.

DETAILED DESCRIPTION OF THE INVENTION

The variables $R^1$, $R^2$, $R^3$ and n in the above general formula are as represented above, the term "radical obtainable by removing the isocyanate groups from 1-isocyanato-3,3,5-trimethyl-5-isocyanato-methyl-cyclohexane", is to be understood to mean a radical of the structure:

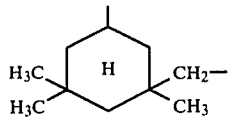

The above-defined radicals $R^1$, $R^2$ and $R^3$ are preferably selected such that (on statistical average) at least about 25% and at the most about 75% of the radicals mentioned represent a hexamethylene radical and n (on statistical average) represents an integer or a fractional number of from about 1 to 5.

Those compounds or mixtures according to the present invention are particularly preferred, wherein (on statistical average) at least about a third and at most about two-thirds of the radicals $R^1$, $R^2$ and $R^3$ represent a hexamethylene radical and n (on statistical average) represents an integer or a fractional number of from about 1 to 3.

As shown by gas chromatographic and/or refractometric experiments on the non-reacted diisocyanate mixtures recovered from the reaction, the ratio of the two radicals in the compounds according to the present invention surprisingly corresponds to the mole ratio of the diisocyanates which are used as a mixture in the present process. Accordingly, in the present process, the diisocyanates mentioned are used in a mole ratio of from about 4:1 to 1:4, preferably from about 3:1 to 1:3, and more preferably from about 2:1 to 1:2.

The compounds or mixtures according to the present invention, in the form of solutions in excess monomeric diisocyanates, are clear, practically colorless, low viscosity liquids. After removing the diisocyanates by known methods, for example by thin layer distillation, the polymers are obtained as practically colorless resins, the content thereof of starting diisocyanates being less than about 5%, by weight, preferably less than about 2%, and more preferably less than about 1%, by weight.

The consistency of the resins depends on the mole ratio of the starting components. The melting point of solid products is generally below about 100° C. and falls with an increasing portion of hexamethylene diisocyanate (HDI). Products having a predominant proportion of HDI are generally liquid at room temperature.

The NCO content of the present products also depends on the composition thereof and is generally from about 12 to 22%, by weight, preferably from about 14 to 21%, by weight.

Gel chromatographic tests provide precise information concerning the composition of the compounds or mixtures according to the present invention. Thus, triisocyanates having one isocyanurate ring (n=1) generally constitute the main component of the monomer-free trimers. Depending on the degree of reaction during production, varying quantities of polyisocyanates having more than one isocyanurate ring (n=2-7) are also present.

The starting materials for the present process are hexamethylene diisocyanate (HDI) and IPDI.

To carry out the process according to the present invention, the mixtures of the starting diisocyanates are subjected to a known trimerization reaction using catalysts accelerating isocyanate trimerization.

All known trimerization catalysts are considered suitable as cataysts for the present process. The following are mentioned as examples of such trimerization catalysts: phosphines, as described in German Offenlegungsschrift No. 1,934,763; alkali metal or lead salts according to British Pat. No. 809,809; alkali metal phenolates (British Pat. Nos. 1,391,066 and 1,386,399); combinations of alkylene oxide and N,N'-endoethylene piperazine ("DABCO") (German Offenlegungsschrift No. 2,644,684 and U.S. Pat. No. 3,211,703); and aziridine or derivatives thereof in combination with a tertiary amine (German Offenlegungsschrift No. 2,825,826).

The use of quaternary ammonium hydroxides corresponding to the following general formula has proved particularly suitable for the present process:

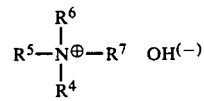

wherein
$R^4$ represents an alkyl radical having from 1 to 20, preferably from 4 to 12 carbon atoms, an araliphatic hydrocarbon radical having from 7 to 10, preferably 7, carbon atoms, or a saturated cycloaliphatic hydrocarbon radical having from 4 to 10, preferably 5 or 6, carbon atoms, each of which may be substituted by hydroxy and/or hydroxyalkyl groups having from 1 to 4 carbon atoms;
$R^5$, $R^6$ and $R^7$, which may be the same or different, represent alkyl radicals having from 1 to 20, preferably from 1 to 4, carbon atoms, which may be hydroxyl-substituted, or two of the radicals $R^5$, $R^6$ and $R^7$, together with the nitrogen atom, optionally together with an oxygen atom or another nitrogen-hetero atom, may form a heterocyclic ring having from 3 to 5 carbon atoms, or $R^5$, $R^6$ and $R^7$ may represent ethylene radicals which, together with the quaternary nitrogen atom and another tertiary nitrogen atom, may form a bicyclic triethylene-diamine ("DABCO")-structure.

Quaternary ammonium hydroxides which are preferred are those corresponding to the above general formula wherein $R^5$, $R^6$ and $R^7$ are as defined above, but with the proviso that at least one of the radicals has at least one aliphatically-bound hydroxyl group which is preferably in the 2-position with respect to the quaternary nitrogen atom, the hydroxyl-substituted radical or the hydroxyl-substituted radicals may have other substituents, in particular $C_1$–$C_4$ alkoxy substituents, in addition to the hydroxyl substituents.

Quaternary ammonium hydroxides which are particularly preferred are those corresponding to the above general formula wherein $R^4$, $R^5$ and $R^6$ represent alkyl radicals of the type mentioned; and $R^7$ represents a hydroxy-ethyl, hydroxy-propyl or hydroxy-butyl radical, the hydroxyl group preferably being in the 2-position with respect to the quaternary nitrogen atoms.

Examples of suitable quaternary ammonium hydroxides include: tetramethyl-, tetraethyl-, trimethylstearyl-, and dimethyl-ethyl-cyclohexyl-ammonium hydroxide; N,N,N-trimethyl-N-(2-hydroxyethyl)-, N,N,N-trimethyl-N-(2-hydroxypropyl)-, and N,N,N-trimethyl-(2-hydroxybutyl)ammonium hydroxide; N,N,-dimethyl-N-dodecyl-N-(2-hydroxyethyl)-ammonium hydroxide; N-(2-hydroxyethyl)-N,N-dimethyl-N-(2,2-dihydroxymethyl-butyl)-ammonium hydroxide; N-methyl-2-hydroxyethyl-morpholinium hydroxide; N-methyl-N-(2-hydroxypropyl)-pyrrolidinium hydroxide; N-dodecyltris-N-(2-hydroxyethyl)-ammonium hydroxide; tetra-(2-hydroxyethyl)-ammonium hydroxide; and compounds corresponding to the following formula:

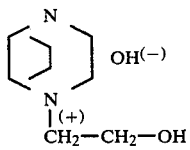

which constitutes the monoadduct of ethylene oxide and water to "DABCO".

The quaternary ammonium hydroxides containing hydroxyalkyl substituents which are preferably used allow a solvent-free trimerization of the diisocyanate mixtures to be used according to the present invention, which, in a good yield, leads to very faintly colored products under easily controllable reaction conditions (immediate commencement of trimerization upon adding the catalyst). Moreover, the catalysts used are thermolabile so that automatic deactivation occurs when certain limiting temperatures are exceeded. As a result of this, the trimerization reaction may be completed with or without using small quantities of a stopper according to the prior art, which has the advantage that clouding does not occur in the product.

The trimerization catalysts are generally used in quantities of from about 0.0001 to 5%, preferably from about 0.001 to 2%, by weight, based on the diisocyanate mixture. When quaternary ammonium hydroxides are used as the catalysts, they are generally used in a quantity of from about 0.0001 to 2%, preferably from about 0.001 to 1%, by weight, based on the diisocyanate mixture used.

When quaternary ammonium hydroxides are used as the catalysts, they are preferably used dissolved in suitable solvents. For example, toluene, dimethyl formamide, dimethyl sulphoxide or mixtures thereof are suitable as solvents and are used in quantities of at most about 5%, by weight, based on the isocyanate mixture used, and are removed by distillation after the reaction, optionally together with the excess diisocyanates.

However, solvents having reactive hydrogen atoms are preferred according to the present invention, in particular alcohols, such as ethanol, propanol, butanols and 2-ethylhexanol, which may react to form carbamic acid derivatives when introduced into the mixture of the diisocyanates to be trimerized and remain in the product.

The simultaneous use of larger quantities of solvents which may be removed by distillation after the reaction, is less preferred according to the present invention.

The present process is carried out at temperatures of from about 20° to 120° C., preferably from about 40° to 100° C.

The process according to the present invention will be exemplified in the following: a mixture of hexamethylene diisocyanate and IPDI is brought to a temperature of from about 20° to 90° C., for example about 50° C., under an inert gas (the use of which is not strictly necessary). The solution of the preferred hydroxyalkyl containing quaternary ammonium hydroxide catalyst is introduced into the reaction solution, whereupon the trimerization reaction commences instantaneously. During the reaction, the temperature rises to from about 60° to 120° C. and may be maintained for example at about 80° C., by suitable measures, at the start of the reaction preferably by cooling, and when the exothermic reaction subsides, by heating. Depending on the quantity of catayst and/or on the reaction temperature, the mixture attains the required NCO value (generally up to a consumption of from about 10 to 60%, preferably from about 10 to 40%, of the NCO groups contained in the starting mixture) within from about 0.5 to 5 hours. The trimerization reaction then stops itself, preferably at reaction temperatures above about 75° C., by thermal deactivation of the catalyst, or may be interrupted by adding a stopper, for example, acids or acid derivatives (perfluorobutane sulphonic acid, benzoic acid, benzoyl chloride, formic acid or 2-ethyl caproic acid), but preferably by heating for a short time to temperatures of from about 80° to 120° C. The trimer solution is then preferably freed from excess monomers under high vacuum, preferably in a thin-layer evaporator and the trimers according to the present invention are obtained as the distillation residue.

The mild course of trimerization is decisive for the quality of the final products (viscosity and color). Therefore, the quantity of catalyst is chosen such that the NCO content is not attained too quickly. For this reason, it may be appropriate only to initiate trimerization, as described above, using a part of the quantity of catalyst, and, after reaching a first temperature maximum, to re-stir the mixture at this temperature until the reaction stops in order then to add more catalyst solution with a renewed increase in temperature taking place. If the required NCO content of the trimer solution has not been reached at this time, the end point may be adjusted according to the same method, using thermolabile catalysts preferably in the range of the specific decomposition temperature thereof. This process may naturally also be carried out in a continuous manner, for example in a stirring vessel cascade.

Surprisingly, when using the quaternary ammonium hydroxides containing hydroxyl groups which are preferably used according to the present invention, an effect is exhibited which stipulates a considerable simplification, particularly when carrying out the process in a continuous manner, even at relatively mild reaction conditions using temperatures below about 100° C. Gas chromatographic and/or refractometric tests of the monomers recovered show that the portion of the individual components is unchanged with respect to the starting mixture; therefore, a stoichiometric reaction has taken place corresponding to the mole ratio of the diisocyanates. Consequently, the diisocyanates recovered may be recycled directly, i.e. without a complex analysis and possible correction of the composition of the diisocyanate mixture.

As shown by gel chromatographic tests of the products, i.e. of the compounds or mixtures according to the present invention, quite predominantly these constitute genuine mixed trimers corresponding to the above general formula and not, for example, mixtures of HDI and IPDI trimers.

On the other hand, the presence of such "homotrimers" in small quantities may naturally not be excluded. The statement that the hydrocarbon radicals of HDI or IPDI in the present compounds are within the limits specified "on statistical average", therefore means that a lowest or highest quantity of hexamethylene diisocyanate together with IPDI in trimerized form is present in the present mixtures, and that is predominantly in the form of genuine mixed trimers.

The compounds or mixtures according to the present invention constitute valuable starting materials for the production of polyurethane plastics according to the polyaddition process, in particular for the production of one- or two-component polyurethane lacquers, and also constitute valuable starting materials for two-component polyurethane stoved enamels in a form blocked with known blocking agents.

Reactants which are preferred for the compounds or mixtures according to the present invention, which may be in a blocked form, in the production of polyurethane lacquers are the following which are known in polyurethane chemistry: polyhydroxy polyesters, polyhydroxy polyethers, polyhydroxy polyacrylates, polycarboxylic acids and optionally low molecular weight, polyhydric alcohols. Polyamines, particularly in a blocked form as polyketimines or oxazolidines, are also suitable reactants for the present mixed polymers.

The quantity ratios are generally selected such that from about 0.8 to 3, preferably from about 0.9 to 1.1, of hydroxy, amino and/or carboxyl groups are allowed per optionally blocked isocyanate group.

In order to accelerate the hardening process, the catalysts conventional in isocyanate chemistry may be used in a known manner, for example, tert. amines, such as triethylamine, pyridine, methylpyridine, benzyl dimethylamine, N,N-endoethylene piperazine, N-methylpiperidine, pentamethyldiethylene triamine, N,N-dimethylaminocyclohexane, N,N'-dimethylpiperazine etc., and metal salts, such as iron (III)-chloride, tin chloride, zinc-2-ethylcaproate, tin (II)-ethylcaproate, dibutyl tin (IV)-dilaurate, molybdenum glycolate, etc.

When using the compounds or mixtures according to the present invention in stoved enamels, the NCO groups thereof are partly or completely blocked in a known manner. For this purpose, the polyisocyanate is reacted with a suitable blocking agent, preferably at an elevated temperature, optionally in the presence of a suitable catalyst (see above).

Blocking agents which are suitable are, for example, the following: monophenols (phenol, cresols), tertiary alcohols (t-butanol, dimethylphenylcarbonol), easy enol-forming compounds (aceto-acetic ester, malonic acid derivatives), secondary aromatic amines, (N-methylaniline, N-phenyl-xylidine), imides, (succinimide), lactams ($\epsilon$-caprolactam, $\delta$-valerolactam), oximes, (butanone oxime, cyclohexanone oxime), mercaptans (methylmercaptan, ethylmercaptan), and triazoles (1H-1,2,4-triazole).

To produce the lacquer binders, the following, for example, optionally blocked polyisocyanates, polyfunctional reactants, catalyst and optionally the conventional additives, for example pigments, fillers and dyes and flowing agents are mixed together thoroughly and homogenized on a conventional mixing apparatus, for example on a sand mill, either with or without a solvent or diluent.

The coating and covering agents may be applied onto the substrate to be coated in solution or from the melt or in a solid form according to conventional methods, for example, coating, rolling, pouring, spraying, by the whirl sintering process or the electrostatic powder spraying process.

When using blocked polyisocyanates in powder lacquers, which are preferably applied according to the electrostatic powder spraying process, it has not been possible hitherto to use HDI only modified by isocyanurate group formation as a powder lacquer hardener; by blocking pure HDI trimers with $\epsilon$-caprolactam in stoichiometric quantities, products which are liquid or sticky at room temperature are obtained and are unsuitable as powder lacquers hardeners due to the low softening point thereof (Comparison Examples 13 and 14), regardless of the trimerization degree and regardless of whether excess monomers are previously removed in an additional stage, for example by thin layer distillation. However, HDI (the portion of which in the mixed trimer, for example, determines the elasticity of the hardened lacquer), may be easily used as a component in powder lacquer hardeners in the form of blocked mixed trimers with cycloaliphatic diisocyanates; HDI-/IPDI mixed trimers blocked with $\epsilon$-caprolactam, for example, are friable and remain pourable for weeks due to the high melting point thereof (Examples 10 to 12). For comparison, a trimer mixture of HDI trimer and IPDI trimer blocked with $\epsilon$-caprolactam (Example 15), shows a clearly narrower melting range in contrast to a mixed trimer of the same overall composition. The ground product sets completely when stored at 40° C.

The mixed trimers of the type according to the present invention, which are low in monomers, have a very desirable solubility and dilutability in conventional lacquer solvents, such as ethyl glycol acetate, ethyl glycol acetate/xylene 1:1, ethyl acetate, butyl acetate, and generally in aromatics and petroleum-rich mixtures of the solvents previously mentioned. Thereby, even highly concentrated solutions exhibit low viscosities. A substantial advantage of the present process may also be seen in the fact that the characteristics of the products may be easily adapted in an optimum manner to the required use by a suitable choice of the mole ratio of the starting diisocyanates. The substantial advantage of the present compounds or mixtures is seen in that the advantages of the purely aliphatic trimers (high elasticity and impact strength of the resulting lacquer) are substantially combined therein with the advantages of the known IPDI trimers (good solubility in non-polar solvents or solvent mixtures, desirable hardness of the lacquer films), but the above-mentioned disadvantages are not included.

The following Examples further illustrate the present invention. All percentages relate to percent, by weight.

The following catalyst solutions are used in the following Examples:

Catalyst A: N-dodecyl-N,N-dimethyl-N-(2-hydroxyethyl)-ammonium hydroxide, prepared by ethoxylating N-dodecyl-N,N-dimethylamine ("Domin") and diluted to an approximately 5% solution using 2-ethyl hexanol/ethanol 8:1

Catalyst B: N-(2-hydroxyethyl)-N,N-dimethyl-N-(2,2-dihydroxymethyl-butyl)-ammonium hydroxide, diluted to an approximately 10% solution using 2-ethyl hexanol Catalyst C: N,N,N-trimethyl-N-(2-hydroxyethyl)-ammonium hydroxide
  I diluted to an approximately 2% solution in 2-ethyl hexanol/ethanol 8:1
  II diluted to an approximately 2% solution in dimethyl formamide/ethanol 8:1
  III diluted to an approximately 6% solution in dimethyl formamide/ethanol 4:1

Catalyst D: N-trimethyl-N-(2-hydroxypropyl)-ammonium hydroxide
  I diluted to an approximately 3% solution in 2-ethyl hexanol/ethanol 8:1
  II diluted to an approximately 6% solution in ethyl hexanol/n-propanol 8:1

EXAMPLE 1

A mixture of 4704 g (28 mols) of hexamethylene diisocyanate and 1554 g (7 mols) of isophorone diisocyanate is mixed with 100 ml of catalyst A at 65° C. The reaction immediately takes place exothermically and is maintained at 80° C. by cooling for 10 minutes. After cooling, the temperature rises to 96° C. After a further 15 minutes, the temperature falls and is maintained at 80° C. by heating. The catalyst is deactivated after a total of 1 hour. The NCO content of the mixture is then constant and amounts to 39.9%. The product which was almost completely freed from monomeric diisocyanates by thin-layer distillation (residual content of HDI: 0.25%, residual content of IPDI: 0.37% has a slight yellowish inherent color, an NCO content of 19.8% and a viscosity of 5320 mPas (23° C.).

EXAMPLE 2

3360 g (20 mols) of HDI and 2220 g (10 mols) of IPDI are mixed with 100 ml of catalyst solution A at 65° C. and the temperature slowly rises to 82° C. When the exothermic reaction dies down, the NCO content of the mixture is 38.5%. A further addition of 30 ml of catalyst solution at 80° C. causes a rise in temperature to 98° C. After a total reaction time of 140 minutes, the catalyst no longer exhibits any activity, the NCO content has fallen to 33.1%. The isocyanate mixture is freed from monomers by thin-layer distillation and dissolved 90% in ethyl glycol acetate/xylene 1:1. The practically colorless solution has an NCO content of 16.6% and a viscosity of 2780 mPas (23° C.).

EXAMPLE 3

444 g (2 mols) of IPDI and 672 g (4 mols) of HDI are mixed with 20 ml of catalyst solution B at 80° C. The reaction immediately takes place exothermically and is maintained at 90° C. by cooling as necessary. After 30 minutes, the reaction is interrupted by adding 1 ml of stopper solution (consisting of 1 ml of perfluorobutane sulphonic acid in 2 ml of dimethyl formamide). The mixture than has an NCO content of 33.6%. A faintly yellow resin is obtained by thin-layer distillation. which, as a practically colorless solution (90%) in ethylene glycol acetate/xylene (1:1), has an NCO content of 16.5%.

EXAMPLE 4

1776 g (8 mols) of IPDI and 2688 g (16 mols) of HDI are mixed with 120 ml of catalyst solution CI at 60° C. The trimerization reaction immediately takes place exothermically, the reaction mixture reaches 75° C. after approximately 10 minutes. After a further 15 minutes, the temperature is 73° C. The reaction is interrupted by adding a solution of 2 ml of perfuorobutane sulphonic acid in 4 ml of dimethyl formamide, when the NCO content is 35.7%. The mixed trimer is obtained by thin-layer distillation in the form of a practically colorless resin having a monomer content of 0.11% of HDI and 0.13% IPDI. The resin has an NCO content of 17.2% and a viscosity of 1350 mPas (23° C.) as a 90% solution in ethyl glycol acetate/xylene 1:1.

EXAMPLE 5

A mixture of 2520 g (15 mols) of HDI and 3330 g (15 mols) of isophorone diisocyanate is first mixed with 100 ml of catalyst solution A and then with 40 ml of this solution at 70° C. During this process, the temperature rises to a maximum of 103° C. After a reaction time of 140 minutes, the NCO content of the solution is 30.8%. The resin obtained by thin-layer distillation is dissolved 80% in ethyl glycol acetate/xylene 1:1. The practically colorless solution has an NCO content of 13.8% and a viscosity of 1440 mPas (23° C.). The content of free HDI is 0.17% and of free IPDI 0.27% (both values based on the solution).

EXAMPLE 6

1344 g (8 mols) of HDI and 3552 g (16 mols) of IPDI are introduced at 65° C. 140 ml of catalyst solution A is added in portions such that the temperature of the solution does not exceed 85° C. at any time. The reaction mixture is then heated to 90° C. and is left for 20 minutes at this temperature. The NCO content of the solution is 31.5%. The resin is freed from diisocyanates by thin-layer distillation and dissolved 80% in ethyl glycol acetate/xylene 1:1.
NCO content: 13.0%
viscosity (23° C.): 930 mPas

EXAMPLE 7

3552 g (16 mols) of IPDI, 1344 g (8 mols) of HDI are mixed with 120 ml of catalyst solution C II at 60° C. The temperature of the mixture rises to 74° C. within 15 minutes and then gradually falls. After a total of 40 minutes, the reaction is stopped by adding a solution of 2 ml of perfluorobutane sulphonic acid in 4 ml of dimethyl formamide and the crude product is subjected to thin-layer distillation. A practically colorless resin is obtained having an NCO content of 13.8% and a viscosity of 1040 mPas (23° C.).

EXAMPLE 8

888 g (4 mols) of IPDI and 336 g (2 mols) of HDI are mixed with 40 ml of catalyst solution C III at 70° C. The temperature of the reaction mixture slowly rises and is maintained at 80° C. initially by cooling as necessary, then by heating. After 15 minutes, the reaction is stopped by adding a solution of 0.5 ml of perfluorobutane sulphonic acid in 1 ml of dimethyl formamide, the NCO content is then 33.2%. The product isolated by thin-layer distillation is dissolved 80% in ethyl glycol acetate/xylene 1:1. The practically colorless product has an NCO content of 13.5%, a viscosity of 620 mPas (23° C.), the content of HDI is 0.16% and the content of IPDI is 0.32%.

EXAMPLE 9

130 ml of catalyst solution A are added in two portions at 70° C. to a mixture of 840 g (5 mols) of HDI and 4440 g (20 mols) of IPDI. After the immediate commencement of the exothermic reaction, the temperature is maintained at 80° C. initially by cooling, and by heating when the exothermic reaction subsides. After a reaction time of 2 hours, the NCO content of the mixture is 30.8%. By heating for 15 minutes to 90° C., remnants of still active catalyst are destroyed, the NCO content is then 30.2%. The product which is low in monomers and obtained by thin-layer distillation has an NCO content of 16.6% and a viscosity of 3780 mPas (23° C.) as an 80% solution in ethyl glycol acetate/xylene 1:1.

EXAMPLE 10

336 g (2 mols) of HDI and 444 g (2 mols) of IPDI are trimerized at 80° C. using a total of 40 ml of catalyst solution D I to an NCO content of 16.8%. The trimer is reacted with 352 g of ε-caprolactam at from 90° to 140° C. The masked trimer melts at from 75° to 81° C. and has a blocked NCO content of 11.6%. The ground product is still pourable after 3 weeks when stored at 40° C.

EXAMPLE 11

168 g (1 mol) of HDI and 444 g (2 mols) of IPDI are mixed with 25 ml of catalyst solution D II at 60° C. The reaction commences immediately in an exothermic manner and is maintained at 80° C. by cooling as necessary. When the exothermic reaction has finished, a further 9 ml of catalyst solution are added and the mixture is maintained at 80° C., initially by cooling and later by heating, until the NCO content is constant. It is then 20.0%.

The mixture is then heated to 100° C. 330 g of molten ε-caprolactam is allowed to drop in with stirring such that the temperature of the mixture gradually rises to 140° C. When the reaction has finished, the mixture is left to cool to room temperature. A brittle, friable solid is obtained which melts at from 92° to 96° C. The NCO content is 0%, the content of blocked isocyanate groups (calculated as NCO) is 13%.

EXAMPLE 12

500 g (2.98 mols) of hexamethylene diisocyanate and 500 g (2.25 mols) of isophorone diisocyanate are mixed with 40 ml of catalyst solution D I at 60° C. The reaction commences immediately and exothermically, the mixture reaches a temperature of 86° C. The temperature is allowed to fall to 80° C. and this temperature is maintained by heating. After a total of 2 hours, the NCO content is 31.5%. After adding more catalyst (25 ml), the mixture reaches a constant NCO content of 16.2% in a further 7 hours at 80° C. The content of free HDI is 6.3%, the content of free IPDI is approximately 6.8%.

Blocking using 436 g of ε-caprolactam at from 100° to 140° C. produces a brittle solid having a melting point of from 72° to 78° C. The content of blocked isocyanate groups 11.3%. The ground solid remains pourable for weeks when stored at 40° C.

EXAMPLE 13

(Comparative Example)

1008 g (6 mols) of HDI are trimerized at 80° C. using a total of 13 ml of catalyst solution D II to an NCO content of 25.5% and are blocked using 692 g of ε-caprolactam at from 100° to 130° C. The cooled product is sticky and cannot be crushed by grinding.

EXAMPLE 14

(Comparative Example)

504 g (3 mols) of HDI are trimerized at 80° C. using 9 ml of catalyst solution D II to an NCO content of 30.0% and freed from monomers by thin-layer distillation (residual monomer content: 0.35%). The NCO content is then 19.5%.

The product is blocked using the stoichiometric quantity of ε-caprolactam at from 100° to 130° C. A product is obtained which is stick at room temperature and cannot be used as a powder lacquer cross-linker.

EXAMPLE 15

(Comparative Example)

93.7 g of monomer-free HDI-trimer, 93.2 g of monomer-free IPDI-trimer, 6.3 g of HDI and 6.8 g of IPDI (corresponding to the composition of the trimer obtained in Example 12) are homogenized at 100° C. The NCO content of the mixture is 20.2%. After blocking using 109 g of ε-caprolactam at from 100° to 140° C., a solid is obtained which melts at from 58° to 65° C. The ground product sets completely when stored at 40° C.

EXAMPLE 16

(Comparative Example)

This Comparative Example shows how far elasticity, impact strength and hardness of lacquers may be varied by using the mixed trimers according to the present invention when the polymer component does not change. In addition thereto, the mixtures specified in the following (details in parts, by weight, NCO:OH=1:1) were prepared from the following starting components:

1. Mixed trimer HDI/IPDI (mol ratio is 2:1) according to Example 4
2. Mixed trimer HDI/IPDI (mol ratio 1:2) according to Example 8
3. IPDI-trimer, 70% in ethyl glycol acetate/xylene 1:1, NCO-content 11.5%, content of free IPDI: <0.7%

Solvent: mixture of equal parts, by weight, of ethyl glycol acetate, xylene, butyl acetate Hydroxyl component: polyesters obtained from adipic acid, hexane diol and diphenyl carbonate, OH content: 6%, by weight Catalyst: "DABCO", 10% dissolved in ethyl glycol acetate (0.5% catalyst, based on the solid resin of the mixture).

| Mixture | A | B | C |
|---|---|---|---|
| Composition | | | |

-continued

| Mixture | A | B | C |
| --- | --- | --- | --- |
| 1 | 86 | — | — |
| 2 | — | 107 | — |
| 3 | — | — | 129 |
| Solvent | 108 | 113 | 88 |
| Polyester | 100 | 100 | 100 |
| Catalyst | 8.8 | 9.3 | 9.5 |

The following was determined on films (approximately 40 μm dry film, spray application, hardening for 14 days at 23° C.) produced therefrom, after complete hardening thereof:

(a) pendulum hardness (according to König; DIN 53 157) in sec
(b) elasticity (DIN 53 156) in mm
(c) impact strength (ASTM D 779-69) in inch×pound.

The following values were determined:

| Film | A | B | C |
| --- | --- | --- | --- |
| a | 74 | 28 | 174 |
| b | 9.5 | 9.2 | 6.9 |
| c | 80 | 80 | 10 |

The results show that films made from the mixed trimers according to the present invention have a clearly improved elasticity and impact strength. Furthermore, it is seen that the hardness of films produced therefrom may be varied in wide limits and may be adapted optimally to a particular use merely by choosing the composition of the present polyisocyanates with otherwise constantly desirable or improved characteristics.

EXAMPLE 17

This Example shows how the characteristics of an alkyd resin lacquer may be improved by using a polyisocyanate according to the present invention.

For this purpose, a commercially available alkyd resin based on soy bean fatty acid (oil length approximately 48% calculated on triglyceride) is dissolved 50% in petroleum and pigmented with titanium dioxide (65% based on the binder).

The characteristics of the films were improved by adding a mixed trimer according to Example 5, which was diluted using petroleum to a 40% solution (8% polyisocyanate, based on solid alkyd resin). The mixture was then diluted using petroleum to processing viscosity. The characteristics of the mixtures or of films produced therefrom are shown in the following Table:

| | | Alkyd resin lacquer without | With a polyisocyanate addition |
| --- | --- | --- | --- |
| Processing time | (1) | unrestricted | 1 working day |
| Pendulum hardness after 16 hours | (2) | 15 sec | 20-30 sec |
| Adhesion after 16 hours | (3) | poor | very good |
| Nail hardness after 16 hours | | poor | good |
| Petroleum resistance | | poor | average |
| Oversprayability | (4) | poor | good |
| Pendulum hardness after 30 days | (2) | approx. 70 sec | approx. 100 sec |
| Gloss | | very good | very good |

(1) Outflow time according to DIN 53 211 using a 4 mm DIN cup, increase from 20 secs. to 35 seconds.
(2) Hardening at 23° C., determination of the damping duration according to König (DIN 53 157).
(3) Test with Tesa crepe band 321, pressed at approximately 500 g, removed after 15 minutes, imprint assessed 30 minutes later.
(4) Films polished after 15 hours and oversprayed with the same lacquer.

EXAMPLE 18

(Comparative Example)

Analogous to the method described in Example 17, the alkyd resin lacquer is mixed with a polyisocyanate. However, in this case a trimer mixture of 43 parts of a pure HDI-trimer and 57 parts of a pure IPDI-trimer are used instead of the HDI/IPDI mixed trimer (mole ratio 1:1, corresponding to a weight ratio of 43:57). Due to the poorer dilutability of the polyisocyanate mixture using petroleum in comparison to that of the mixed trimer, a cloudy solution is obtained when diluted to the same solids content as in Example 28. The films obtained exhibit a considerable impairment in the gloss degree after drying at room temperature or at 60° C.

EXAMPLE 19

The following Table describes the difference in the resin character of "pure" trimers, trimer mixtures and a mixed trimer according to the present invention:

| Polyisocyanate | Resin Character at 23° C. |
| --- | --- |
| HDI-trimer | liquid |
| HDI/IPDI-mixed trimer Weight ratio 43:57 according to Example 5 | viscous |
| HDI/IPDI-trimer mixture Weight ratio 43:57 | solid, soft |
| IPDI-trimer | solid, brittle |

It is shown in the following how these differences are reflected in the elasticity of two-component polyurethane lacquers, based on these polyisocyanates.

For this purpose, the four isocyanate types specified were combined with a conventional polyacrylate resin of acrylic acid, methacrylic esters and styrene modified with a hard polyester (60% in xylene, 3.5% OH groups based on solids) and were pigmented with titanium dioxide (65% based on total binder). Films produced therefrom were hardened for 20 days at room temperature. The Erichsen drawing assessment was then determined in mm (layer thickness of the films approximately 40 μm).

| Polyisocyanate component | Erichsen-drawing (mm) |
| --- | --- |
| HDI-trimer | 7-9 |
| Mixed trimer | 6-7 |
| Trimer-mixture | 0.5-1 |
| IPDI-trimer | 0.5-0.8 |

Due to the greater soft resin character of the mixed trimer, the lacquer film produced therefrom exhibits an elasticity which is adequate for practical purposes, while the corresponding trimer mixture takes the elasticity from the lacquer.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Compounds or mixtures of compounds corresponding to the following general formula:

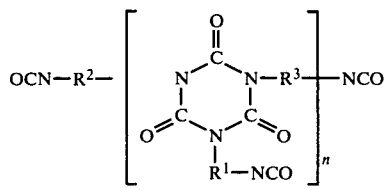

wherein
$R^1$, $R^2$ and $R^3$, which may be the same or different, represent a hexamethylene radical or a radical obtainable by removing the isocyanate groups from 1-isocyanato-3,3,5-trimethyl-5-isocyanatomethyl-cyclohexane, such that (on statistical average) at least about 20% and at the most about 80% of the radicals $R^1$, $R^2$ and $R^3$ represent a hexamethylene radical; and n represents an integer, or based on statistical average, a fractional number of from about 1 to 7.

2. The compounds or mixtures of compounds according to claim 1 wherein based on statistical average at least about 25% and at most about 75% of the radicals $R^1$, $R^2$ and $R^3$ represent a hexamethylene radical.

3. The compounds or mixtures of compounds according to claim 1 wherein based on statistical average at least about a third and at most about two-thirds of the radicals $R^1$, $R^2$ and $R^3$ represent a hexamethylene radical.

4. A process for the preparation of compounds or mixtures of compounds according to claim 1, comprising trimerizing a portion of the isocyanate groups of a diisocyanate mixture consisting of aliphatic and cycloaliphatic diisocyanates in the presence of catalysts, accelerating the trimerization of isocyanate groups, stopping the trimerization reaction as soon as from about 10 to 60% of the isocyanate groups which were originally present are trimerized, deactivating the catalyst used by heating the reaction mixture to a temperature above the decomposition temperature of the catalyst and/or by adding a catalyst poison, and optionally removing the non-reacted excess isocyanate by thin-layer distillation, characterized in that a mixture of hexamethylene diisocyanate and 1-isocyanato-3,3,5-trimethyl-5-isocyanatomethyl-cyclohexane is used in a mole ratio of from about 4:1 to 1:4.

5. The process according to claim 4, characterized in that the diisocyanates are used in a mole ratio of from about 3:1 to 1:3.

6. The process according to claim 4, characterized in that the diisocyanates are used in a mole ratio of from about 2:1 to 1:2.

7. The process according to claim 4, 5 or 6, characterized in that quaternary ammonium hydroxides are used as the catalyst.

8. The process according to claim 7, characterized in that quaternary ammonium hydroxides having at least one hydroxy-alkyl group bound to nitrogen is used as the catalyst.

9. Isocyanurates containing isocyanate groups which are prepared by
   (a) trimerizing a mixture comprising hexamethylene diisocyanate and 1-isocyanato-3,3,5-trimethyl-5-isocyanatomethyl-cyclohexane in a molar ratio of from about 4:1 to 1:4 in the presence of a trimerization catalyst,
   (b) terminating the reaction after about 10 to 60% of the isocyanate groups initially present have been trimerized by deactivating the catalyst either by heating the reaction mixture to a temperature above the decomposition temperature of the catalyst and/or by adding a catalyst poison and
   (c) optionally removing the unreacted excess diisocyanate by thin-layer distillation.

10. The isocyanurates of claim 9 which are prepared by trimerizing a mixture comprising hexamethylene diisocyanate and 1-isocyanato-3,5,5-trimethyl-5-isocyanatomethyl-cyclohexane in a molar ratio of from about 3:1 to 1:3.

11. The isocyanurates of claim 9 which are prepared by trimerizing a mixture comprising hexamethylene diisocyanate and 1-isocyanato-3,5,5-trimethyl-5-isocyanatomethyl-cyclohexane in a molar ratio of about 2:1 to 1:2.

12. The isocyanurates of claim 9 which are prepared by using a quaternary ammonium hydroxide as the catalyst.

13. The isocyanurates of claim 12 wherein said quaternary ammonium hydroxide contains at least one hydroxyalkyl group bound to a nitrogen atom.

* * * * *